US012765986B2

(12) United States Patent
Wisgerhof et al.

(10) Patent No.: US 12,765,986 B2
(45) Date of Patent: Oct. 20, 2026

(54) METHOD OF EVALUATING AN EMBOLIC FILTER

(71) Applicant: EmStop Inc., Brainerd, MN (US)

(72) Inventors: Taylor Wisgerhof, New Hope, MN (US); David Feddema, Maple Grove, MN (US); Mark Groh, Fairview, NC (US)

(73) Assignee: EmStop Inc., Brainerd, MN (US)

( * ) Notice: Subject to any disclaimer, the term of this patent is extended or adjusted under 35 U.S.C. 154(b) by 517 days.

(21) Appl. No.: 18/141,826

(22) Filed: May 1, 2023

(65) Prior Publication Data

US 2023/0346535 A1 Nov. 2, 2023

Related U.S. Application Data

(60) Provisional application No. 63/337,320, filed on May 2, 2022.

(51) Int. Cl.

| | |
|---|---|
| ***A61F 2/01*** | (2006.01) |
| ***A61M 5/00*** | (2006.01) |
| *A61B 90/00* | (2016.01) |

(52) U.S. Cl.

CPC ............. *A61F 2/013* (2013.01); *A61M 5/007* (2013.01); *A61B 2090/376* (2016.02); *A61B 2090/378* (2016.02); *A61M 2210/127* (2013.01)

(58) Field of Classification Search

CPC . A61F 2/01; A61F 2/013; A61M 5/00; A61M 5/007; A61M 2210/127

See application file for complete search history.

(56) References Cited

U.S. PATENT DOCUMENTS

| | | | | |
|---|---|---|---|---|
| 9,895,452 B2 * | 2/2018 | Hohn | .................. | A61L 24/0031 |
| 2015/0110722 A1 * | 4/2015 | Hohn | ................ | A61K 49/0457 424/9.44 |

* cited by examiner

*Primary Examiner* — Vi X Nguyen

(74) *Attorney, Agent, or Firm* — Kilpatrick Townsend & Stockton LLP

(57) ABSTRACT

Aspects described herein are directed to methods of evaluating an embolic filter. A method for evaluating an embolic filter includes positioning the embolic filter in a blood vessel. A measured quantity of radiopaque particulates is injected into the blood vessel upstream of the embolic filter. An efficacy of the embolic filter is determined via invitro imaging of the embolic filter and the radiopaque particulates.

20 Claims, 14 Drawing Sheets

METHOD OF EVALUATING AN EMBOLIC FILTER

CROSS REFERENCE TO RELATED APPLICATION DATA

The present application claims the benefit under 35 USC § 119(e) of U.S. Provisional Appln. No. 63/337,320 filed May 2, 2022; the full disclosure which is incorporated herein by reference in its entirety for all purposes.

BACKGROUND

Some medical procedures that are performed at a treatment site within a patient's vasculature have a substantial risk of dislodging embolic material. To address the risk of dislodging embolic material, an embolic filter may be deployed downstream of the treatment site to capture dislodged embolic material. One such medical procedure is transcatheter aortic valve replacement (TAVR). TAVR is a proven strategy for the treatment of severe aortic stenosis that has been validated for use in patients who are not eligible for surgical aortic valve replacement (SAVR) due to patient frailty or associated high operative risk. TAVR with the use of a self-expanding or balloon-expanded bioprosthetic valve has been FDA-approved for commercial use in the US in selected patients. TAVR is rapidly becoming the method of choice to treat aortic stenosis in patients deemed to be at increased risk of death if offered a traditional surgical aortic valve replacement.

Although results have been encouraging with TAVR, the risk of stroke has been demonstrated to be significantly higher with TAVR relative to SAVR. Clinically observed stroke (CVA) underestimates the prevalence of embolic events inherent with TAVR. During TAVR, stent and implanted valve expansion (with or without the use of a balloon) results in native valve compression and radial leaflet displacement that leads to the liberation of tissue and particulate matter that travels distally in the arterial tree. Some of the debris lodges in terminal branches of cerebral vessels and will be evidenced with new onset stroke. Other debris released at the time of TAVR lodge in vessels of the peripheral circulation, renal circulation, coronary circulation, and mesenteric circulation. These patients may manifest clinical scenario of renal failure, mesenteric ischemia, peripheral ischemia, and/or myocardial infarction. Other patients may not have acute clinical deterioration but may suffer late effects due to impaired functional reserve related to sub-clinical embolic events. The occurrence of embolic events during TAVR is a significant impediment to offering the technique to larger lower risk groups of patients.

In view of the potential of dislodged embolic material to cause substantial harm, it is important that an embolic material have a high efficacy in capturing embolic material. Thus, there is a need for systems and methods to assist a user in assessing the efficacy of the embolic filter within the blood vessel, to improve overall effectiveness of the embolic filter and to limit the occurrence of embolic events, such as during TAVR procedures.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embolic filters are an important feature of a variety of cardiac surgical procedures in which embolic material may be dislodged into the blood stream. Such filters can prevent a variety of complications associated with such procedures, as the embolic material is captured and collected to avoid stroke and other substantial health risks.

While a variety of design considerations have been recently developed to increase the efficacy of the embolic filter, including material and dimensional considerations which allow for more flexible adaption of the geometry of the embolic filer within the blood vessel, these considerations do not entirely prevent risks of failure or poor performance of the embolic filter in the event of poor placement and positioning.

As such, the embolic filter evaluation system, described herein, presents a system and accompanying method to evaluate the embolic filter, to determine the embolic filter's overall efficacy, such as prior to the liberation of embolic material into the blood stream. The system described provides a visual technique in which radiopaque particulates can be released into the blood stream and allowed to flow through the blood vessel while being visualized by the user (such as the physician or technician). Such particulates, as harmless if not captured within the embolic filter, allow for a "trial run" of the embolic filter to ensure its ability to successfully capture embolic material.

In some aspects, such evaluation of the embolic filter may be performed manually by a user by visually evaluating the radiopaque particulates, as visually displayed to the user. In other aspects, the embolic filter evaluation system may utilize processing systems which allow for automated or semi-automated detection and analysis of the positioning and capture (or lack thereof) of radiopaque particulates within the embolic filter, in order to provide specific numerical (or graphical) indications of the efficacy of the embolic filter. These indications may provide a quantifiable understanding to the user of the efficacy of the filter, and allow the user to make determinations of whether the embolic filter is suitably positioned to safely proceed with the cardiac procedure (such as a TAVR procedure).

In some embodiments, the embolic filter evaluation system includes a radiopaque particulate introducer. The radiopaque particulate introducer may be used to provide radiopaque particulates into the blood flow within the heart to test the effectiveness of the embolic filter. For example, the radiopaque particulates may be introduced into the blood flow prior to a valve replacement procedure, such as an aortic valve replacement procedure, such that the embolic filter is tested prior to embolic material being liberated from the aortic valve during valve replacement.

In some embodiments, the radiopaque particulate introducer may be configured for insertion through an access location in the heart. The radiopaque particulate introducer may be a transapical introducer. In particular, the radiopaque particulate introducer may be inserted through the through the left ventricle and through the annular plane of the aortic valve, such that the distal end of the radiopaque particulate introducer is within the aorta. In various implementations, the access location may be the same opening within the heart which is utilized to position the embolic filter (such as via an embolic filter catheter), or may be used exclusively for insertion of the radiopaque particulate introducer. The proximal end of the radiopaque particulate introducer may include a syringe having a syringe body and a plunger. Radiopaque particulates may be positioned within the syringe body prior to injection of the particulates into the heart. According to various aspects, the radiopaque particulates may be mixed within a liquid, such as saline or a saline mixture.

In one aspect, the embolic filter evaluation system may include an imagery system. The imagery system may include at least one imagery device which is capable of imaging the radiopaque particulates as the particulates are injected out of the radiopaque particulate introducer and into the aorta. For example, the imagery may be a video recording created for a time-frame corresponding with the time of injection and capture of the radiopaque particulate. As such, the imagery may convey an image (or images) or video which may include imagery of the heart and the radiopaque particulates within the aorta. The imaging device may include a fluoroscope or echocardiograph, for example.

In some embodiments, the imaging device may be coupled with a computer to provide the imagery to the computer. The computer may include a processor configured to receive the imagery, and may further include various filtering and processing features to process the imagery received by the computer. For example, the processor may be coupled with a display, which may visually display to a user an image or video of the aorta 106 and radiopaque particulates. In particular, the display may show a video of the radiopaque particulates being injected within the aorta.

In some embodiments, the computer may further include a memory configured to store data. In particular, the memory may store the imagery provided by the imaging device. Furthermore, the memory may be configured to receive user input data, including, for example, historical information, and/or operating parameters, including information regarding the quantity of radiopaque particulates injected into the heart.

The processor may further be configured to analyze the imagery provided by the imaging device, such that the computer may provide efficacy data for determining the overall performance of the embolic filter in capturing the radiopaque particulate. For example, the processor may be configured to detect the amount of radiopaque particulates captured within the embolic filter and/or the processor may be configured to detect the amount of radiopaque particulates which is not captured within the embolic filter (i.e. that has escaped). The processor may then compare the amount captured, or the amount that escaped, to the overall amount which was injected to determine an efficacy of the embolic filter.

In another aspect, a method for evaluating an embolic filter includes positioning an embolic filter in a blood vessel. In some embodiments the method includes injecting radiopaque particulates into the blood vessel upstream of the embolic filter. For example, injecting may occur from positioning a distal end of an introducer upstream from the embolic filter, and injecting the radiopaque particulates into the blood vessel through the introducer.

In some embodiments, the method may include determining an efficacy of the embolic filter at capturing the radiopaque particulates by imaging the embolic filter and the radiopaque particulates in the blood vessel. For example, the method may include measuring the amount of particulates injected into the blood vessel. The method may include measuring an amount of radiopaque particulates captured by the embolic filter, and/or an amount of radiopaque particulates which bypass the embolic filter. Thus, the amount of radiopaque particulates captured or the amount which bypass the embolic filter may be compared to the amount of radiopaque particulates injected into the blood vessel to determine the efficacy of the embolic filter. In various embodiments, only one of: (i) measuring an amount of the radiopaque particulates captured by the embolic filter; and (ii) measuring an amount of the radiopaque particulates which bypass the embolic filter, are performed. In various embodiments, both measuring steps above may be performed, such as to provide two separate calculations of the efficacy of the embolic filter.

For a fuller understanding of the nature and advantages of the present invention, reference should be made to the ensuing detailed description and accompanying drawings.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
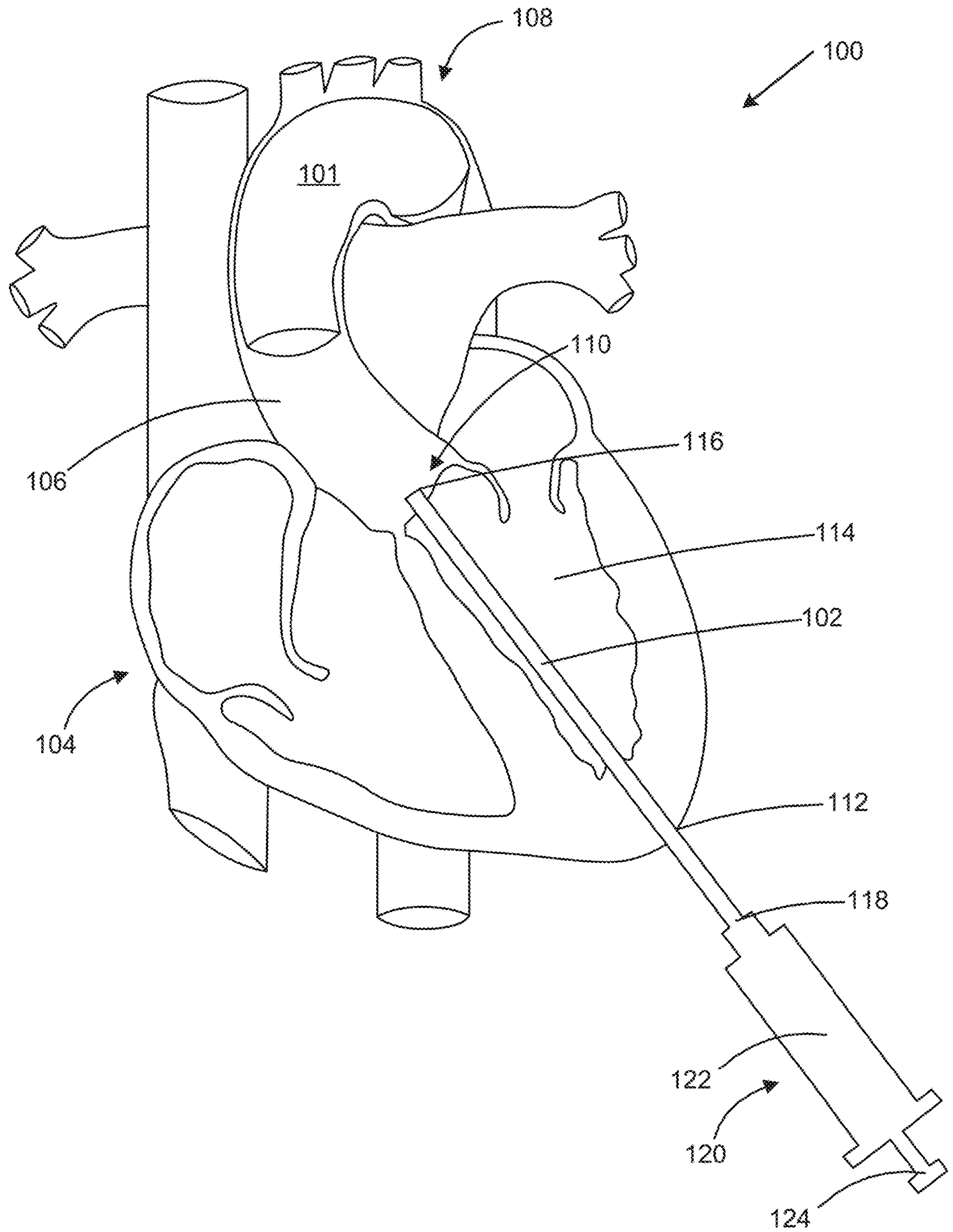
FIG. 1 shows a side cross-sectional view of an embodiment of an embolic filter evaluation system that includes an embolic filter and a radiopaque particulate introducer.

Referring now to the drawings, in which like reference numerals represent like parts throughout the several views, FIG. 1 illustrates aspects of a embolic filter evaluation system 100 according to various aspects of the present disclosure, including an embolic filter 101 (also referred to as an embolic material filter assembly) and a radiopaque particulate introducer 102.

According to various implementations, the embolic filter evaluation system 100 may include an embolic filter 101 being positioned within a blood vessel of the heart 104. For example, the blood vessel may be the aorta 106. In particular, the embolic filter 101 may be positioned within the aortic arch 108. Such positioning may allow for the filtration of embolic material which is liberated from the aortic valve 110, such as during an aortic valve replacement procedure. As such, as blood flows through the aortic valve 110 and though the aorta 106, the embolic filter 101 may capture such embolic material, as discussed previously. While the embolic filter evaluation system is illustrated and discussed in the context of procedures related to aortic valve replacement, it should be understood that the embolic filter evaluation system 100 may be utilized for other cardiac procedures, and particularly for replacement procedures of other heart valves.

According to various implementations, the embolic filter evaluation system 100 may include a radiopaque particulate introducer 102. The radiopaque particulate introducer 102 may be used to provide radiopaque particulates (not shown) into the blood flow to test the effectiveness of the embolic filter 101. For example, the radiopaque particulates may be provided into the blood prior to a valve replacement procedure, such that the embolic filter 101 is tested prior to embolic material being liberated from the aortic valve 110.

The radiopaque particulate introducer 102 may be a transapical introducer, which is provided through an access location 112 in the heart 104. In particular, the radiopaque particulate introducer 102 may be inserted through the through the left ventricle 114 and through the annular plane of the aortic valve 110, such that the distal end 116 of the radiopaque particulate introducer 102 is within the aorta 106. In various implementations, the access location 112 may be the same opening within the heart 104 which is utilized to position the embolic filter 101 (such as via an embolic filter catheter). In various implementations, the access location 112 may be used only for inserting the radiopaque particulate introducer 102 within the heart 104. The proximal end 118 of the radiopaque particulate introducer 102 may include a syringe 120 having a syringe body 122 and a plunger 124. Radiopaque particulates may be positioned within the syringe body 122 prior to injection of the particulates into the heart 104. According to various aspects, the radiopaque particulates may be mixed within a liquid, such as saline or a saline mixture to allow for ease of injection within the heart 104. Example particulate that can be used is Titanium and 304 Stainless Steel in sizes ranging from 120 micron to 255 micron in diameter. Particulate in diameters outside of 120 micron to 255 micron in diameter may be used when testing filters with small pore sizes. Any suitable quantity of particulate can be injected. For example, in many embodiments, the quantity of particulate injected can range from 2 grams up to 50 grams. In some embodiments, the quantity of particulate injected can range from 10 grams to 20 grams.

Figure 2:
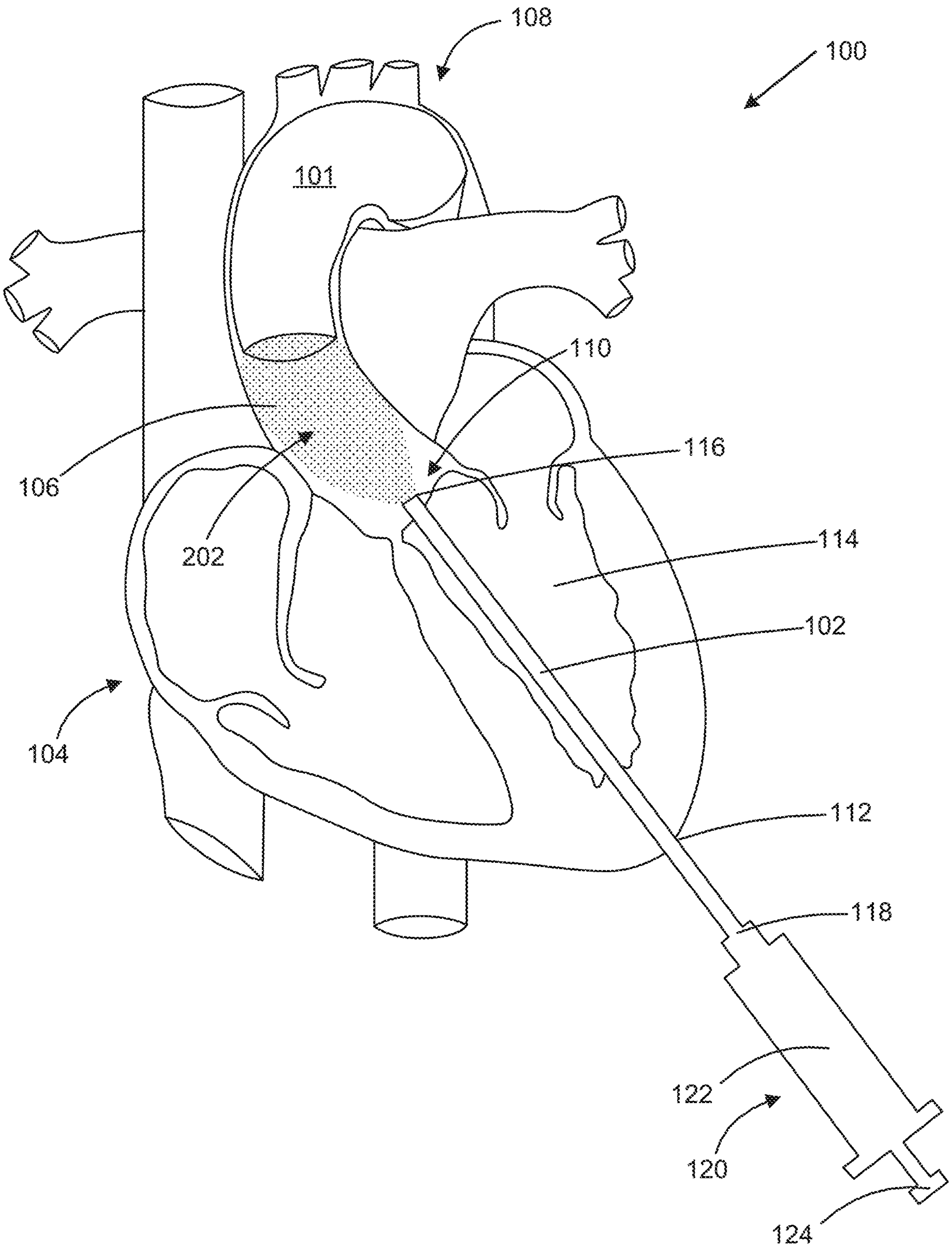
FIG. 2 shows a side cross-sectional view of the embolic filter evaluation system of FIG. 1 that includes radiopaque particulates deployed within the aorta.

FIG. 2 illustrates the embolic filter evaluation system 100 of FIG. 1 after the radiopaque particulates 202 are injected out of the distal end 116 of the radiopaque particulate introducer 102 and into the aorta 106, according to various implementations of the disclosure. For example, a user may compress the plunger 124 of the syringe 120 such that a saline-particulates mixture (including the radiopaque particulates 202) is forced to and out of the distal end 116 of the radiopaque particulate introducer 102 and into the aorta 106. In particular, the distal end 116 may be positioned proximal to the annular plane of the aortic valve 110. Upon release of the radiopaque particulates 202 from the radiopaque particulate introducer 102, the radiopaque particulates 202 may flow within the blood flow towards the aortic arch 108.

Figure 3:
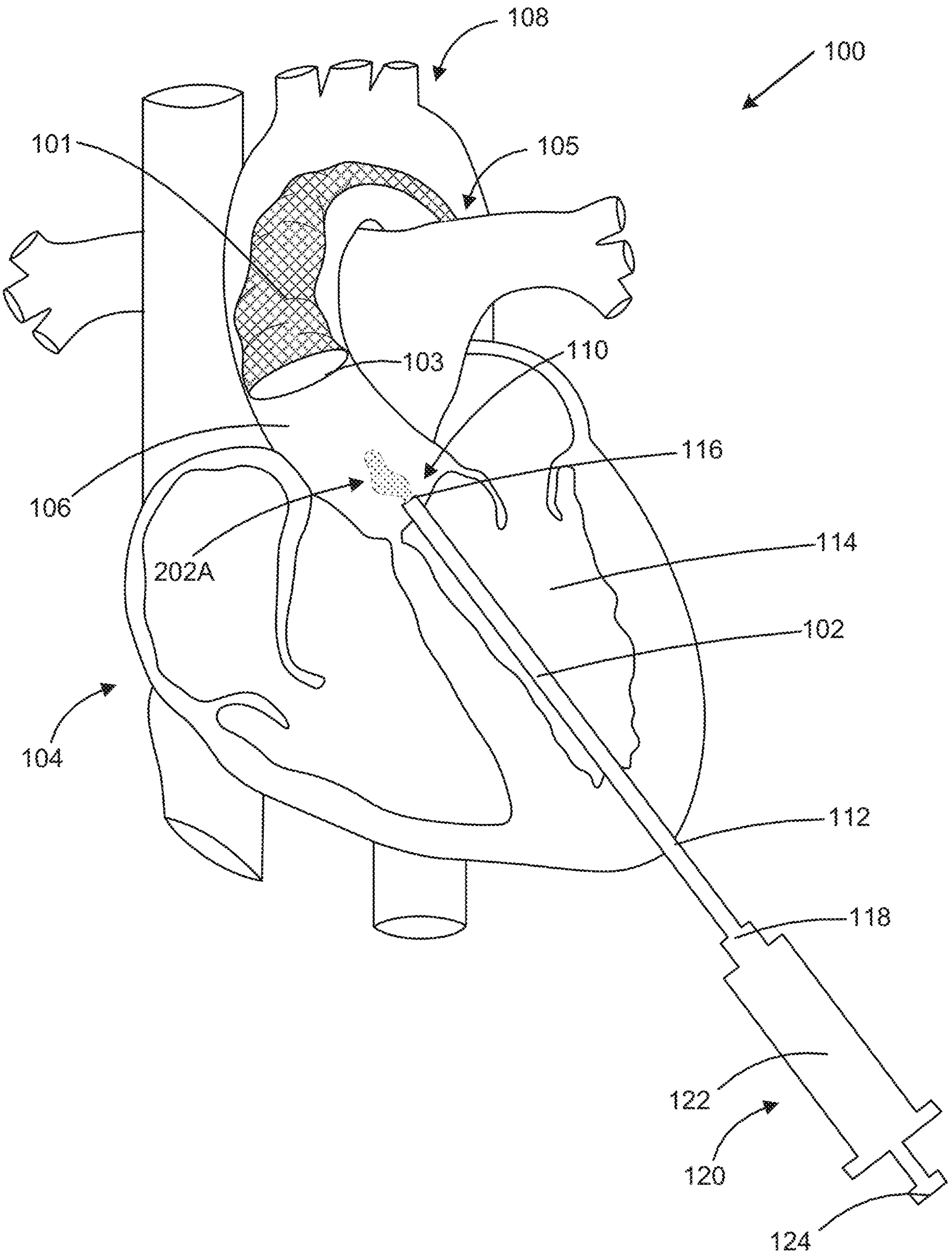
FIG. 3 shows a side cross-sectional view of an embodiment of an embolic filter evaluation system that includes an embolic filter and a radiopaque particulate introducer, where the radiopaque particulates are introduced within the aorta.
Figure 4:
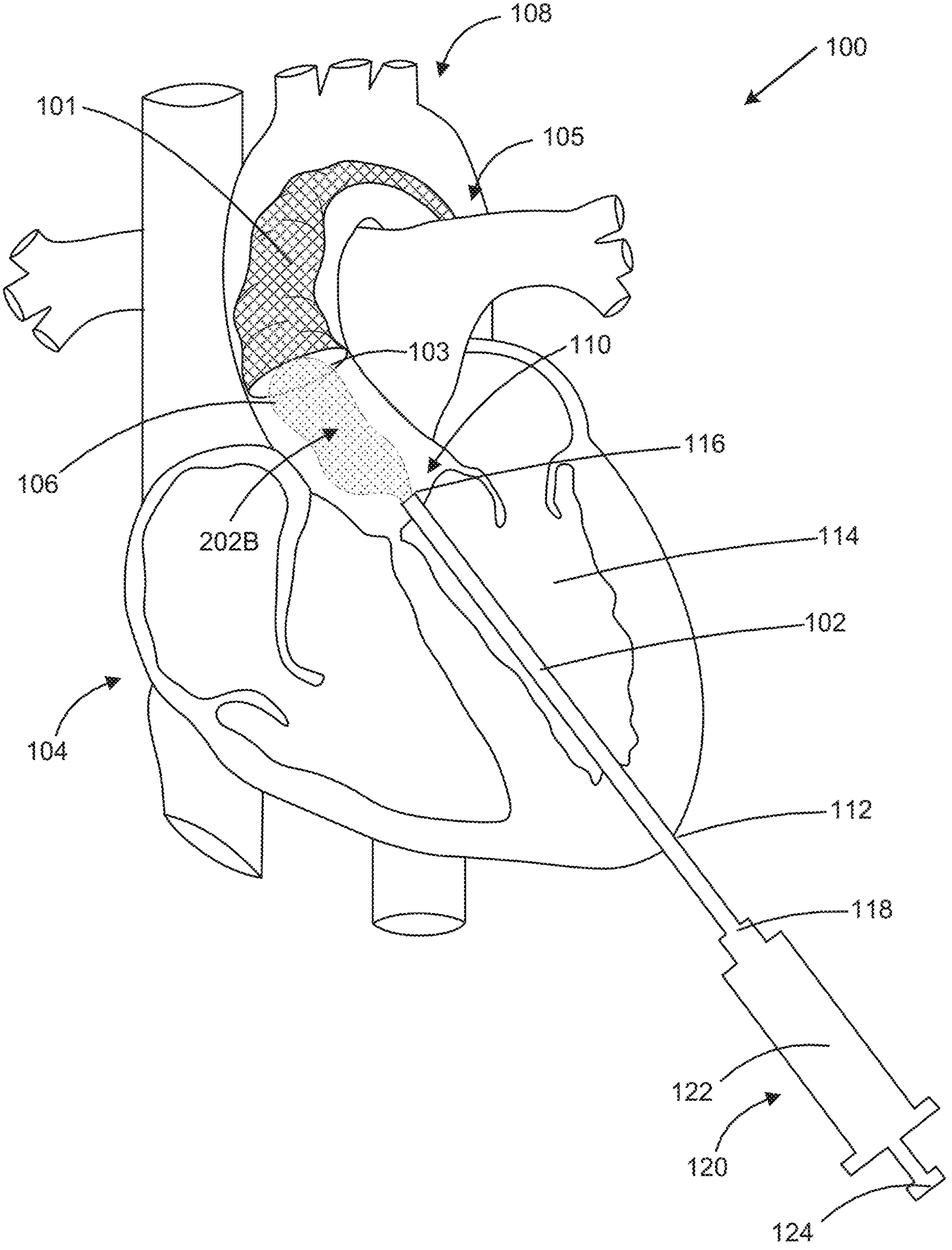
FIG. 4 shows a side cross-sectional view of the embolic filter evaluation system of FIG. 3 that includes radiopaque particulates approaching the opening of the embolic filter at the distal end portion.
Figure 5:
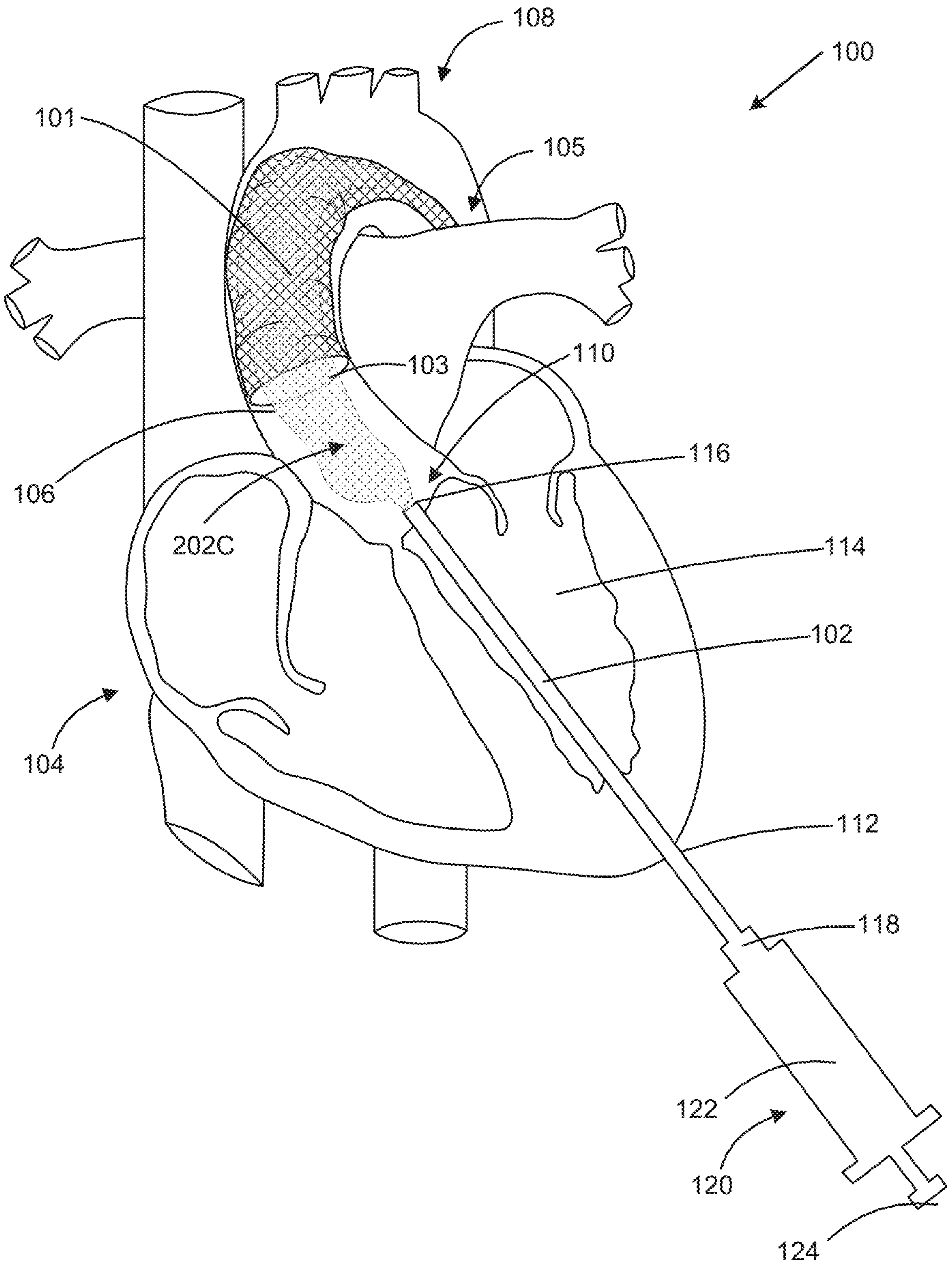
FIG. 5 shows a side cross-sectional view of the embolic filter evaluation system of FIG. 3 that includes radiopaque particulates entering into the embolic filter.

FIGS. 3-5 illustrate the advancement of the radiopaque particulate 202 as it flows out of the distal end 116 of the radiopaque particulate introducer 102 towards the embolic filter 101. The embolic filter 101 may be configured to conform to the shape of the blood vessel between a distal end portion 103 and the proximal end portion 103 of the embolic filter 101 (e.g., to the curvature of the aorta 106 or aortic arch 108). The distal end portion 103 of the embolic filter 101 may have a diameter (when in the expanded position) to contact each side of the aorta 106, such as to prevent or minimize embolic material from passing the opening in the embolic filter 101 at the distal end portion 103. According to various implementations, the embolic filter 101 may have a generally tapered structure, such that an outer scaffold of the embolic filter has a larger diameter at the distal end portion 103 than the proximal end portion 103. Specific details of an exemplary embolic filter 101 are discussed below in FIGS. 10-14.

FIG. 3 illustrates the embolic filter evaluation system 100 immediately after radiopaque particulates 202A exits the distal end 116 of the radiopaque particulate introducer 102. FIG. 4 shows the embolic filter evaluation system 100 of FIG. 3 with the radiopaque particulates 202B approaching the opening of the embolic filter 101 at the distal end portion 103. FIG. 5 shows the embolic filter evaluation system 100 of FIG. 3 with radiopaque particulates 202C entering into the embolic filter 101 and being captured therein. If the embolic filter 101 is functioning at complete efficiency, all of the radiopaque particulates 202C is captured within the embolic filter 101. However, a portion of the radiopaque particulates 202C may escape past the opening at the distal end portion 103 of the embolic filter 101 and proceed through the aortic arch 108. Analysis and detection of what portion of the radiopaque particulates 202C is or is not captured within the embolic filter 101 may provide information regarding the performance of the embolic filter 101, as discussed below.

Figure 6:
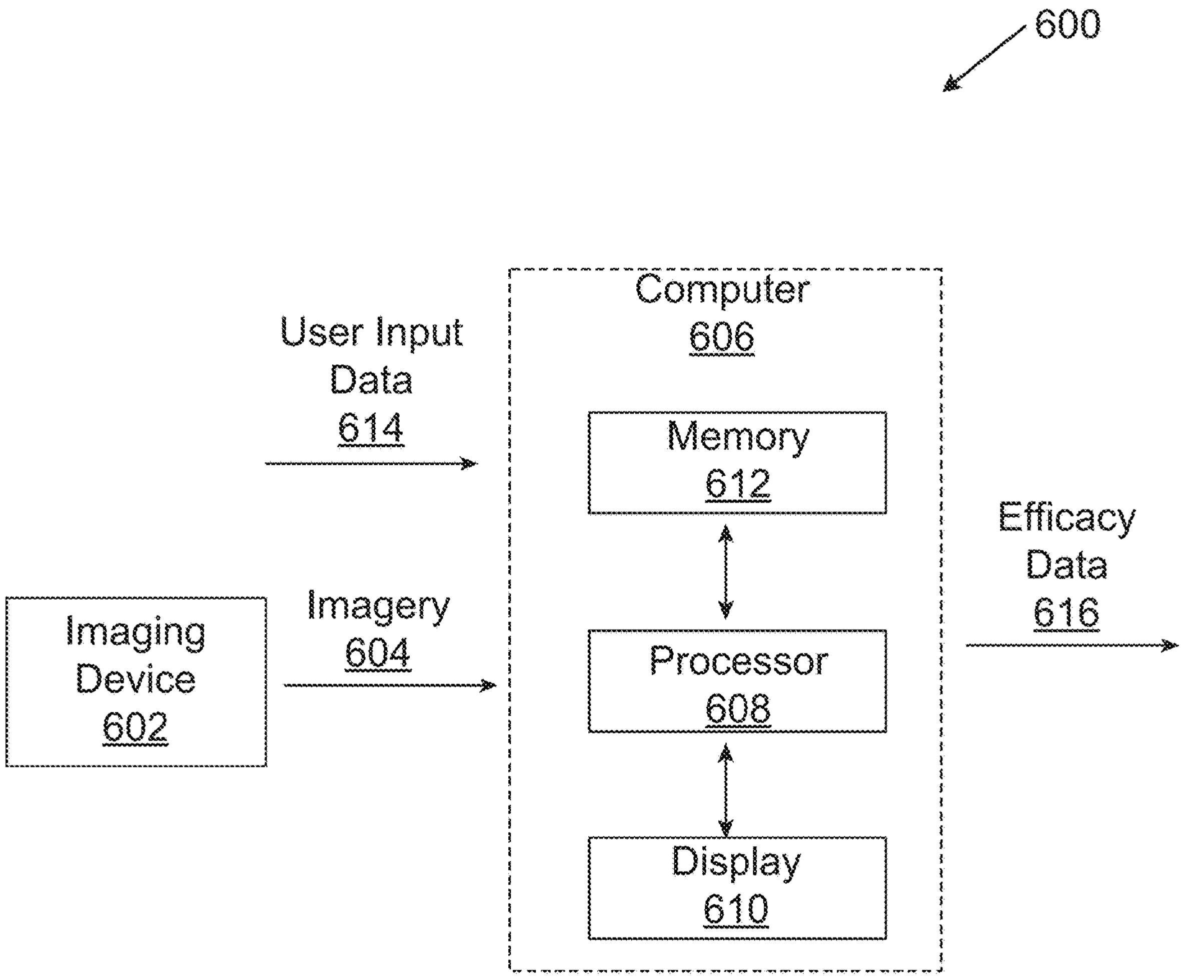
FIG. 6 shows an exemplary system architecture of an imagery system of the embolic filter evaluation system.

FIG. 6 illustrates an exemplary system architecture of an imagery system 600 of the embolic filter evaluation system 100, according to various aspects of the present disclosure. The imagery system 600 may include at least one imagery device 602 which is capable of imaging the radiopaque particulates 202. The imaging device 602 may be configured to be positioned near the heart 104, such as externally of the patient in the heart region, and collect imagery 604 as the particulates are injected out of the radiopaque particulate introducer and into the aorta 106. For example, the imagery 604 may be a video recording created for a time-frame corresponding with the time of injection and capture of the radiopaque particulates 202. As such, the imagery 604 may convey an image (or images) or video which includes imagery of the heart and the radiopaque particulates 202 within the aorta 106. The imaging device 602 may include a fluoroscope or echocardiograph for example, although other devices which are capable of imaging or detecting the radiopaque particulates 202 may also be used.

The imaging device 602 may be communicatively coupled with a computer 606, and configured to provide the imagery 604 to the computer 606. The computer 606 may include a processor 608 configured to receive the imagery 604, and may further include various filtering and processing features to process the imagery 604 received by the computer 606. For example, the processor may be coupled with a display 610, which may visually display to a user an image or video of the aorta 106 and radiopaque particulates 202. In particular, the display 610 may show a video of the radiopaque particulates 202 being injected within the aorta 106 in real-time.

The computer 606 may further include a memory 612 configured to store data. In particular, the memory 612 may store the imagery 604 provided by the imaging device 602. For example, the memory 612 may store the imagery 604, such that the imagery 604 can be reviewed (i.e., re-watched) such that a user can view the imagery multiple times, as need be, to analyze function of the embolic filter 101. Furthermore, the memory may be configured to receive user input data 614, including, for example, historical information, and/or operating parameters, including information regarding the quantity of radiopaque particulates 202 injected into the heart 104. Such user input data 614 may be provided via the display 610, which may be a graphical display or user interface, for example.

The processor 608 may further be configured to analyze the imagery 604 provided by the imaging device 602, such that the computer 606 may provide efficacy data 616 determining the overall performance of the embolic filter 101 in capturing the radiopaque particulate. For example, the processor 608 may be configured to detect the amount of radiopaque particulates 202 captured within the embolic filter 101 and/or the processor 608 may be configured to detect the amount of radiopaque particulates 202 which is not captured within the embolic filter (i.e. that has escaped). The processor 608 may then compare the amount captured (or the amount that escaped) to the overall amount which was injected into the heart 104 to determine an efficacy of the embolic filter 101. From this, the processor 608 may provide to the user, information identifying the efficacy of the embolic filter. Such efficacy data 616 may be provided in a variety of formats, including a numerical representation (e.g., a ratio or percentage) or a graphical representation, which may utilize graphical elements, including graphs or charts, color-coding, or other display features to identify to the user an overall determination of the capability and efficacy of the embolic filter.

Figure 7:
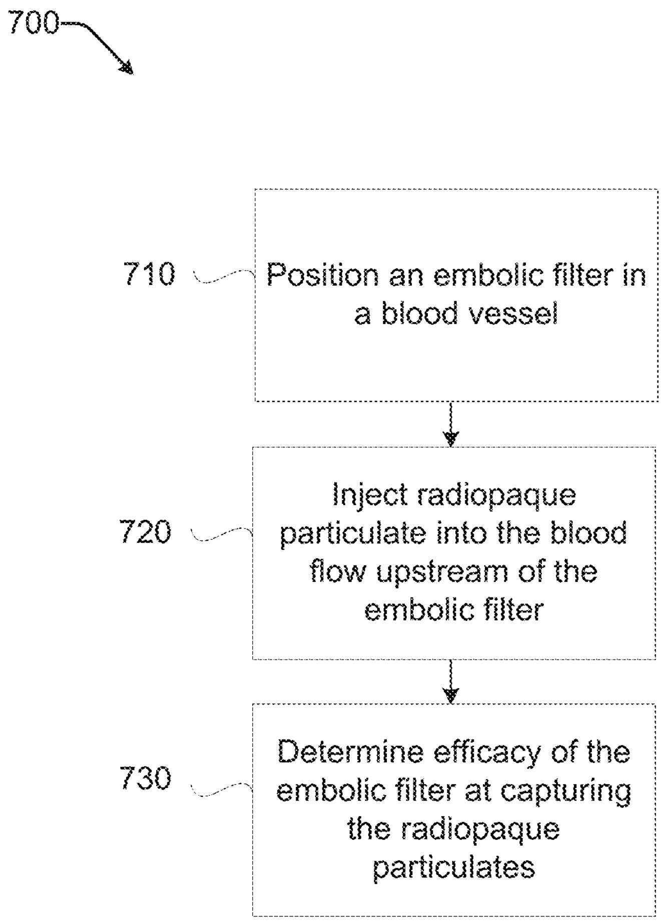
FIG. 7 shows a flowchart of an exemplary process associated with systems and methods of evaluating an embolic filter.
Figure 8:
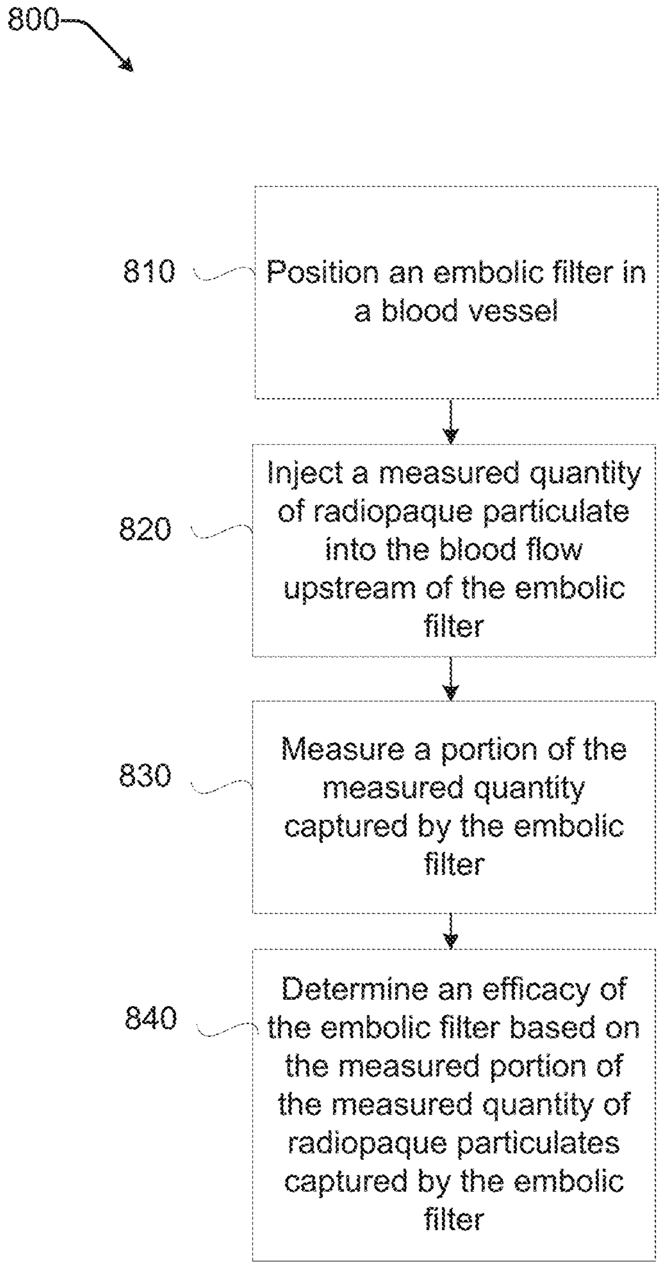
FIG. 8 shows a flowchart of an exemplary process associated with systems and methods of evaluating an embolic filter.
Figure 9:
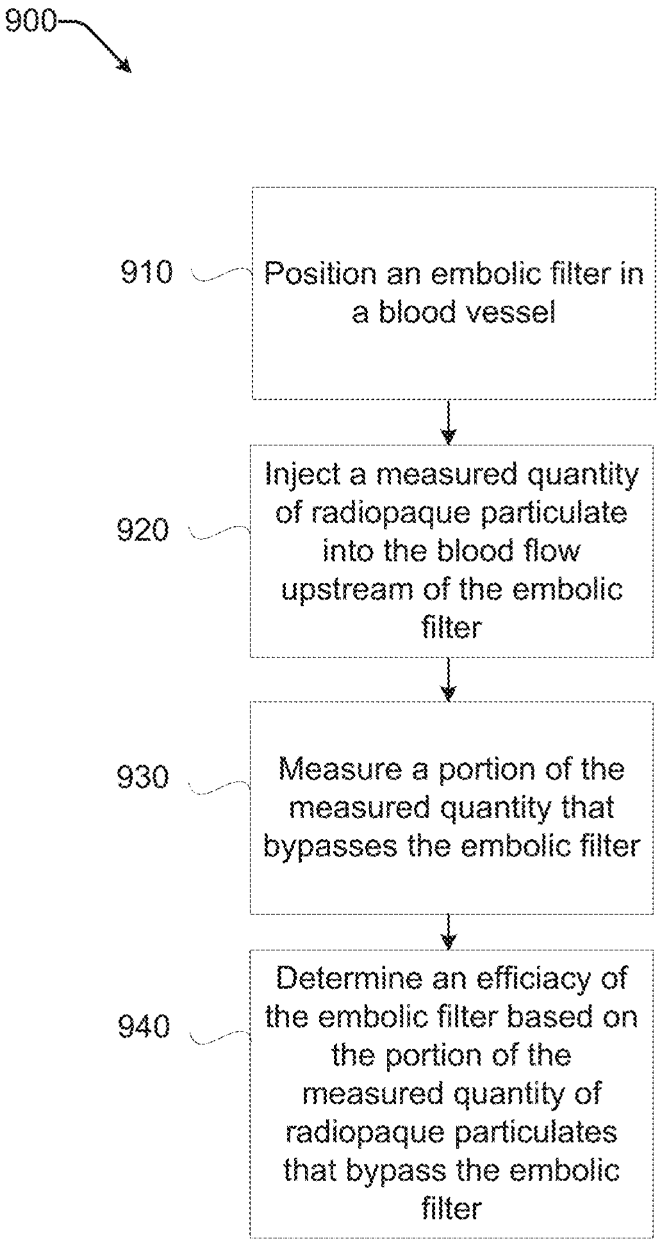
FIG. 9 shows a flowchart of an exemplary process associated with systems and methods of evaluating an embolic filter.

FIGS. 7-9 show methods of evaluating an embolic filter.

FIG. 7 is a flowchart of an exemplary process 700 associated with systems and methods of evaluating an embolic filter (e.g., embolic filter 101). In some implementations, one or more process blocks of FIG. 7 may be performed by a computer system (e.g., computer 606). Additionally or alternatively, one or more blocks of FIG. 7 may be performed manually, such as by an operator, user, technician, physician, or the like.

At block 710, the process 700 may include positioning an embolic filter (e.g., embolic filter 101) in a blood vessel. The blood vessel may be the aorta 106, and specifically within the aortic arch 108, or may be another blood vessel of the body, and/or another chamber of the heart 104. Positioning the embolic filter within the blood vessel may be provided with use of a variety of medical procedures, including surgical cardiac procedures and trans catheter procedures. In particular, embolic filter catheter devices may be used for insertion and placement of the embolic filter. In various implementations, positioning the embolic filter may include inserting the embolic filter into a vasculature comprising the blood vessel though an access site.

At block 720, the process 700 may include injecting radiopaque particulates (e.g., radiopaque particulates 202) into the blood vessel upstream from the embolic filter. Injecting may include positioning a distal end of an introducer (e.g., radiopaque particulate introducer 102) upstream from the embolic filter and injecting the radiopaque particulates into the blood vessel through the introducer. Positioning of the introducer may include performing a partial sternotomy to provide transapical access to the heart, and may include inserting the distal end of the introducer into the heart, such as through the transapical access. Positioning of the distal end of the introducer may also include inserting the introducer through the vasculature through the access site. The access site may be the same access site as the access site of the embolic filter, above. Injecting radiopaque particulates, may include injecting a mixture of a saline solution and the radiopaque particulates into the blood vessel.

At block 730, the process 700 may include determining an efficacy of the embolic filter at capturing the radiopaque particulates by imaging the embolic filter and the radiopaque particulates in the blood vessel. Imaging the embolic filter and the radiopaque particulates in the blood vessel may include fluoroscopic imaging (e.g., with an imaging device 602 comprising a fluoroscope). Imaging the embolic filter and the radiopaque particulates in the blood vessel may include echocardiographic imaging (e.g., with an imaging device 602 comprising an echocardiograph). Imaging the embolic filter and the radiopaque particulates in the blood vessel may include imaging at least a portion of the radiopaque particulates entering the embolic filter. Imaging the embolic filter and the radiopaque particulates in the blood vessel may include imaging capture of at least a portion of the radiopaque particulates by the embolic filter.

The process 700 may further include measuring an amount of the radiopaque particulates injected into the blood vessel, and may further include measuring an amount of the radiopaque particulates captured by the blood filter by evaluating images generated via the imaging of the embolic filter and the radiopaque particulates in the blood vessel (e.g., via the imaging device 602).

The process 700 may further include measuring an amount of the radiopaque particulates injected into the blood vessel, and may further include measuring an amount of radiopaque particulates that bypass the embolic filter by evaluating images generated via the imaging the embolic filter and the radiopaque particulates in the blood vessel (e.g., via the imaging device 602).

FIG. 8 is a flowchart of an exemplary process 800 associated with systems and methods of evaluating an embolic filter (e.g., embolic filter 101). In some implementations, one or more process blocks of FIG. 8 may be performed by a computer system (e.g., computer 606). Additionally or alternatively, one or more blocks of FIG. 8 may be performed manually, such as by an operator, user, technician, physician, or the like.

At block 810, the process 800 may include positioning an embolic filter (e.g., embolic filter 101) in a blood vessel. The blood vessel may be the aorta 106, and specifically within the aortic arch 108, or may be another blood vessel of the body, and/or another chamber of the heart 104. Positioning the embolic filter within the blood vessel may be provided with use of a variety of medical procedures, including surgical cardiac procedures and trans catheter procedures. In particular, embolic filter catheter devices may be used for insertion and placement of the embolic filter. In various implementations, positioning the embolic filter may include inserting the embolic filter into a vasculature comprising the blood vessel though an access site.

At block 820, the process 800 may include injecting a measured quantity of radiopaque particulates (e.g., radiopaque particulates 202) into the blood vessel upstream from the embolic filter. Injecting may include positioning a distal end of an introducer (e.g., radiopaque particulate introducer 102) upstream from the embolic filter and injecting the radiopaque particulates into the blood vessel through the introducer. Positioning of the introducer may include performing a partial sternotomy to provide transapical access to the heart, and may include inserting the distal end of the introducer into the heart, such as through the transapical access. Positioning of the distal end of the introducer may also include inserting the introducer through the vasculature through the access site. The access site may be the same access site as the access site of the embolic filter, above. Injecting radiopaque particulates, may include injecting a mixture of a saline solution and the radiopaque particulates into the blood vessel.

At block 830, the process 800 may include measuring a portion of the measured quantity of radiopaque particulates captured by the embolic filter by imaging the embolic filter and the radiopaque particulates in the blood vessel. Imaging the embolic filter and the radiopaque particulates in the blood vessel may include fluoroscopic imaging (e.g., with an imaging device 602 comprising a fluoroscope). Imaging the embolic filter and the radiopaque particulates in the blood vessel may include echocardiographic imaging (e.g., with an imaging device 602 comprising an echocardiograph).

At block 840, the process 800 may include determining an efficacy of the embolic filter based on the portion of the measured quantity of radiopaque particulates captured by the embolic filter. For example, determining may include comparing the measured portion of the measured quantity of radiopaque particulates to the (overall) measured quantity of the radiopaque particulates, to determine a percentage or what portion of the radiopaque particulates are captured within the embolic filter.

The process 800 may include presenting the determined efficacy (e.g., efficacy data 616) of the embolic filter to a user (or operator). The determined efficacy may be provided in a variety of formats, including a numerical representation (e.g., a ratio or percentage) or a graphical representation, which may utilize graphical elements, including graphs or charts, color-coding, or other display features to identify to the user an overall determination of the capability and efficacy of the embolic filter.

FIG. 9 is a flowchart of an exemplary process 1300 associated with systems and methods of evaluating an embolic filter (e.g., embolic filter 101). In some implementations, one or more process blocks of FIG. 9 may be performed by a computer system (e.g., computer 606). Additionally or alternatively, one or more blocks of FIG. 9 may be performed manually, such as by an operator, user, technician, physician, or the like.

At block 910, the process 900 may include positioning an embolic filter in a blood vessel. The blood vessel may be the aorta 106, and specifically within the aortic arch 108, or may be another blood vessel of the body, and/or another chamber of the heart 104. Positioning the embolic filter within the blood vessel may be provided with use of a variety of medical procedures, including surgical cardiac procedures and trans catheter procedures. In particular, embolic filter catheter devices may be used for insertion and placement of the embolic filter. In various implementations, positioning the embolic filter may include inserting the embolic filter into a vasculature comprising the blood vessel though an access site.

At block 920, the process 900 may include injecting a measured quantity of radiopaque particulates (e.g., radiopaque particulates 202) into the blood vessel upstream from the embolic filter. Injecting may include positioning a distal end of an introducer (e.g., radiopaque particulate introducer 102) upstream from the embolic filter and injecting the radiopaque particulates into the blood vessel through the introducer. Positioning of the introducer may include performing a partial sternotomy to provide transapical access to the heart, and may include inserting the distal end of the introducer into the heart, such as through the transapical access. Positioning of the distal end of the introducer may also include inserting the introducer through the vasculature through the access site. The access site may be the same access site as the access site of the embolic filter, above. Injecting radiopaque particulates, may include injecting a mixture of a saline solution and the radiopaque particulates into the blood vessel.

At block 930, the process 900 may include measuring a portion of the measured quantity of radiopaque particulates that bypasses the embolic filter by imaging the embolic filter and the radiopaque particulates in the blood vessel. Imaging the embolic filter and the radiopaque particulates in the blood vessel may include fluoroscopic imaging (e.g., with an imaging device 602 comprising a fluoroscope). Imaging the embolic filter and the radiopaque particulates in the blood vessel may include echocardiographic imaging (e.g., with an imaging device 602 comprising an echocardiograph).

At block 940, the process 900 may include determining an efficacy of the embolic filter based on the portion of the measured quantity of radiopaque particulates that bypasses the embolic filter. For example, determining may include comparing the measured portion of the measured quantity of radiopaque particulates that bypasses the filter to the (overall) measured quantity of the radiopaque particulates, to determine a percentage or what portion of the radiopaque particulates bypassed the embolic filter.

The process 900 may include presenting the determined efficacy (e.g., efficacy data 616) of the embolic filter to a user (or operator). The determined efficacy may be provided in a variety of formats, including a numerical representation (e.g., a ratio or percentage) or a graphical representation, which may utilize graphical elements, including graphs or charts, color-coding, or other display features to identify to the user an overall determination of the capability and efficacy of the embolic filter.

Figure 10:
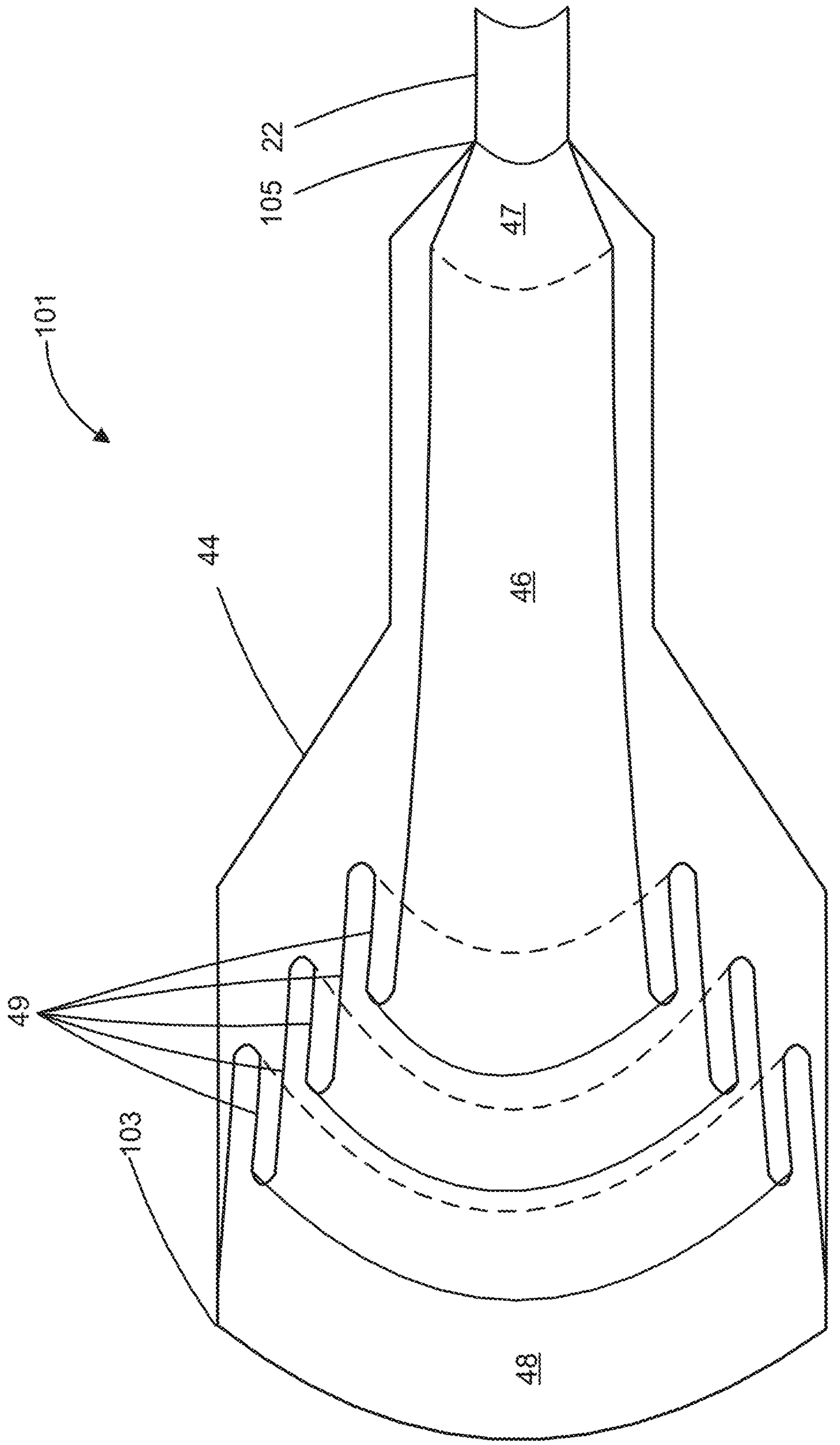
FIG. 10 shows a side cross-sectional view of an embodiment of an embolic filter that includes a pleated inner filter that accommodates axial contraction of an outer scaffold of the embolic filter during deployment.

FIG. 10 illustrates an exemplary embolic filter 101, including an outer scaffold 44 that is configured to self-expand from an insertion configuration to a deployed configuration, in which an outer surface of the embolic filter 101 engages a blood vessel. Further details relating to the deployment of the embolic filter 101 can be found in co-assigned and concurrently filed U.S. Provisional Appln No. 63/337,340, which is hereby incorporated by reference in its entirety.

In many embodiments, the embolic filter 101 includes the outer scaffold 44 and an inner filter 46 attached to the outer scaffold. The outer scaffold 44 can include one or more members that radially expand into contact with the wall of a vessel along which embolic material is blocked from traversing. The inner filter 46 can include a filtering device or filtering membrane configured to prevent emboli of greater than a particular size from passing through the filtering device or the filtering membrane. For example, to capture emboli greater than or equal to 200 microns in size, the inner filter 46 can have apertures of 200 microns or less in size. To provide for a suitable pressure drop across the inner filter 46 in use, the inner filter 46 can have apertures between a suitable minimum size (e.g., 50 microns) and a suitable maximum size (e.g., 200 microns) for capturing emboli greater than or equal to 200 microns in size. In some embodiments, the inner filter 46 has 140 micron apertures to provide a suitable balance between size of emboli captured and a suitable pressure drop across the inner filter 46 in use. The outer scaffold 44 is configured to provide a framework and stability for the inner filter 46 to function.

In many embodiments, the inner filter 46 has a suitable porosity that provides for capture of embolic material by the inner filter 46 while accommodating blood flow through the inner filter 46. The inner filter 46 can be made from any suitable material. For example, in some embodiments, the inner filter 46 includes a helically-braided polyethylene terephthalate (PET) filter. In some embodiments, the inner filter 46 includes a helically-braided polymer filter made from a suitable polymer yarn such as ultra-high-molecular-weight polyethylene (UHMWPE), PET, nylon, polypropylene, polytetrafluoroethylene (PTFE), and liquid crystal polymer (LCP). In some embodiments, the inner filter 46 includes a laser cut polymer filter made from a suitable polymer material (e.g., elastomeric materials such as silicones, polyurethanes and co-polymers). In some embodiments, the inner filter 46 includes a woven textile filter with a diameter less than or equal to the braided outer scaffold 44 with target porosity to capture embolic material and allow for blood flow through the inner filter 46. Such a woven textile filter can be made from a suitable polymer yarn such as UHMWPE, PET, nylon, polypropylene, PTFE, and LCP. The inner filter 46 can have any suitable configuration. For example, in many embodiments, the inner filter 46 can have an outer diameter in the fully deployed configuration less than or equal to the inner diameter of the outer scaffold 44 in the fully deployed configuration. In many embodiments, the inner filter 46 has a longitudinal length and/or longitudinal flexibility that accommodates the change in length of the outer scaffold 44 between the insertion configuration and the fully deployed configuration.

In many embodiments, the embolic filter 101 has a flexibility so as to have a deployed shape in which the distal end of the embolic filter 101 conforms to the inner surface of the blood vessel (e.g., the aorta) and conforms to the shape of the blood vessel. For example, in many embodiments, the embolic filter 101 is configured to conform to the shape (e.g., curvature) of the blood vessel between the distal end portion 103 of the embolic filter 101 and the proximal end portion 103 (e.g., to the curvature of the aorta).

Figure 11:
FIG. 11 is a picture of a prototype of the pleated inner filter of FIG. 10.
Figure 12:
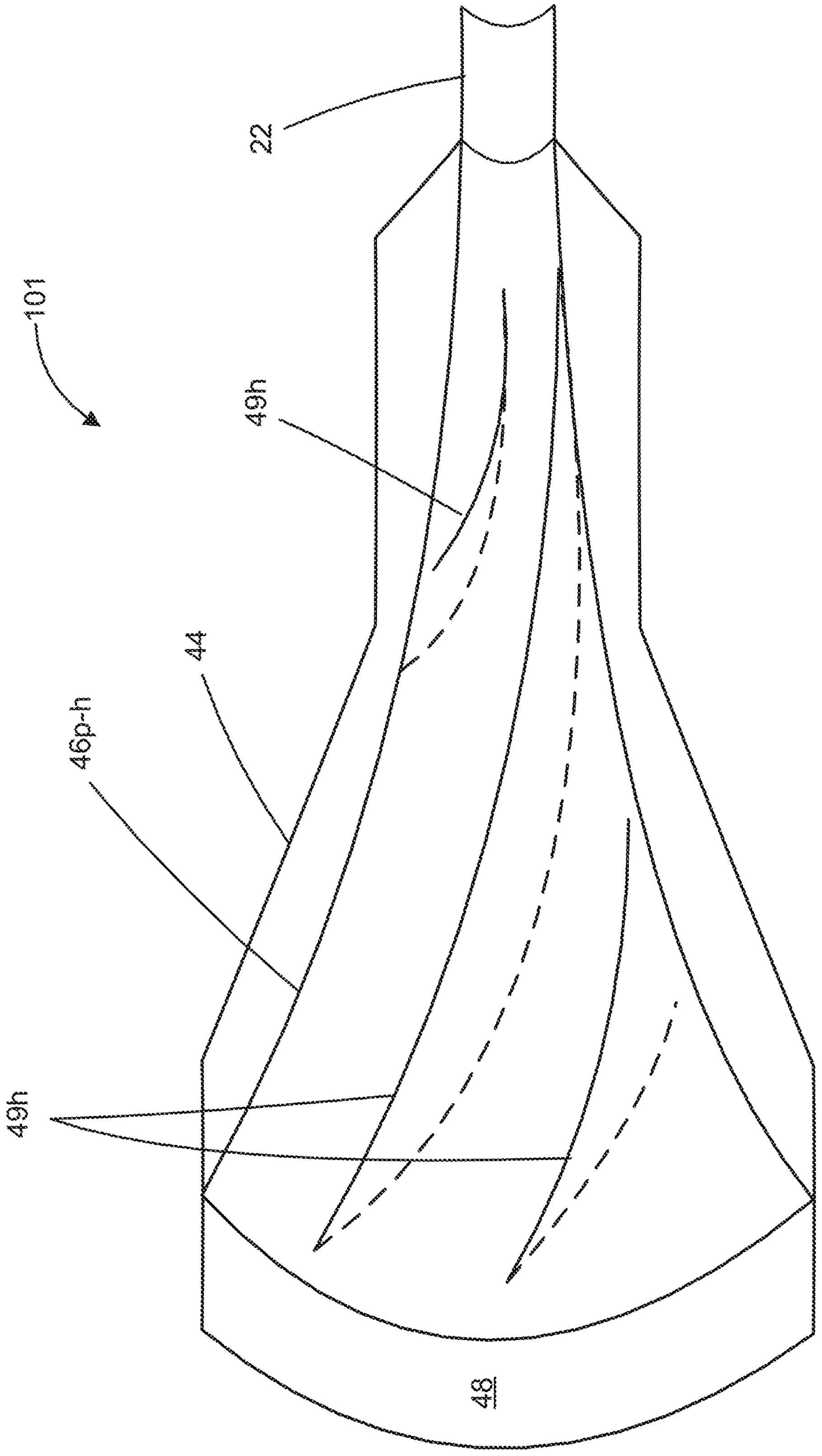
FIG. 12 shows a side cross-sectional view of an embodiment of the embolic filter that includes a helically-pleated inner filter that accommodates axial contraction of the outer scaffold of the embolic filter during deployment.
Figure 13:
FIG. 13 is an end-view picture of a prototype of the helically-pleated inner filter of FIG. 12.

In some embodiments of the embolic filter 101, the inner filter 46 has pleats 49 in the deployed configuration that accommodate contraction of the outer scaffold 44 during deployment of the embolic filter 101 from the insertion configuration to the deployed configuration. FIG. 10 shows a side cross-sectional view of an embodiment of the embolic filter 101 that includes an inner filter 46 with pleats 49 in the deployed configuration as illustrated. The inner filter 46 can be configured to have the pleats 49 in the deployed configuration using any suitable approach. For example, the pleats 49 can be formed in the inner filter 46 using heat setting such that, in the absence of axial tension applied to the inner filter 46 by the outer scaffold 44 in the insertion configuration, the inner filter 46 has an unrestrained configuration that includes the pleats 49. FIG. 11 is a picture of a prototype of the pleated inner filter 46 in the unrestrained configuration. FIG. 12 shows a side cross-sectional view of an embodiment of the embolic filter 101 that includes an inner filter 46*p-h* with helical pleats 49*h* in the deployed configuration as illustrated. The inner filter 46*p-h* can be configured to have the helical pleats 49*h* in the deployed configuration using any suitable approach. For example, the helical pleats 49*h* can be formed in the inner filter 46*p-h* using heat setting such that, in the absence of axial tension applied to the inner filter 46*p-h* by the outer scaffold 44 in the insertion configuration, the inner filter 46*p-h* has an unrestrained configuration that includes the helical pleats 49*h*. FIG. 13 is a picture of a prototype of the helically-pleated inner filter 46*p-h* in the deployed configuration of the embolic filter 101.

Figure 14:
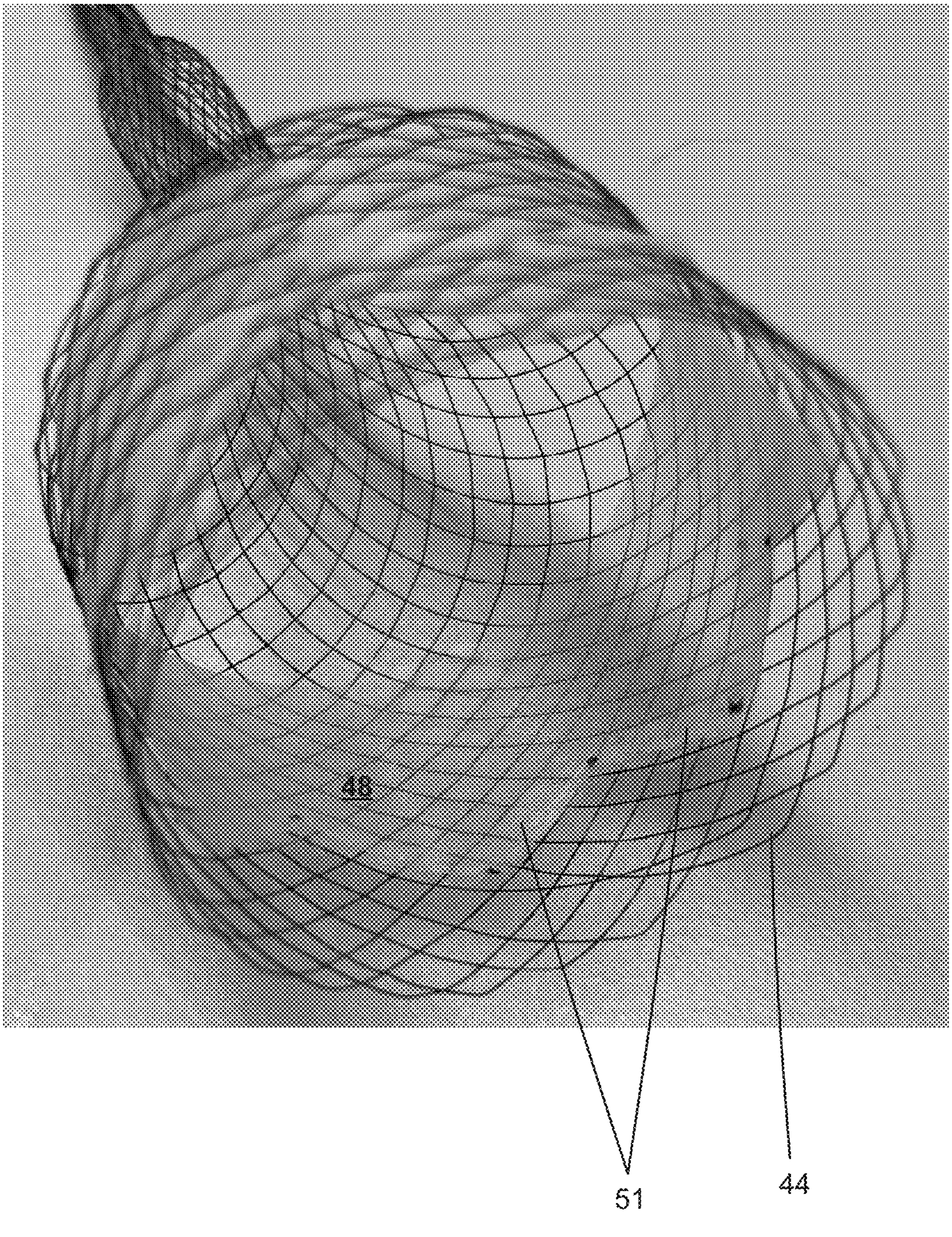
FIG. 14 is a picture of an embodiment of the embolic filter that includes an outer scaffold and an inner filter distal end portion with a zig-zag shaped distal end that is aligned with and attached to a weave of the outer scaffold.

FIG. 14 is a picture of an embodiment of the embolic filter 101 that includes the outer scaffold 44 and an embodiment of the inner filter 46 with a zig-zag shaped distal end 51. The zig-zag shaped distal end 51 is aligned with and woven into the braid of the outer scaffold 44 to secure the distal end 51 to the outer scaffold 44 so as to inhibit passage of emboli around the inner filter 46 and to minimize the resulting combined thickness of the embolic filter 101 at the distal end 51 of the inner filter 46. In some embodiments, the inner filter 46 includes a non-pleated distal end member 48 that includes the distal end 51, and further includes a pleated member that attached to the proximal end of the non-pleated distal end member 48 and extends to the inner sheath 22.

The devices and methods described herein are expected to produce substantial benefits in the way of substantially increased safety and efficacy of surgical treatments with a high likelihood of generation of embolic material, such as aortic valve replacement. As a result, such surgical treatments may be performed on a substantially increased number of patients with improve outcomes and reduce recovery times. Specifically, there will be less embolic material conveyed within the circulation system, thereby lowering the incidence of clinical stroke, subclinical stroke, silent cerebral embolization, renal embolization, mesenteric embolization, and peripheral embolization and each of the associated clinical syndromes.

The embolic filter evaluation system 100 is suitable for use in procedures involving covered or uncovered stenting of arteries for capture and extraction of embolic material that may be liberated during their implantation for the treatment of aneurysms, dissections, stenosis or thrombus. The embolic filter evaluation system 100 is suitable for prevention of injury resulting from embolic events occurring during balloon aortic valvuloplasty. The embolic filter evaluation system 100 is suitable for prevention of tissue injury resulting from the performance of mitral balloon valvuloplasty or replacement.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of evaluating an embolic filter, the method comprising:

positioning an embolic filter in a blood vessel, wherein the embolic filter is configured to remove embolic material from a flow of blood passing through the blood vessel;

injecting radiopaque particulates into the flow of blood passing through the blood vessel, wherein the radiopaque particulates are injected into the flow of blood upstream of the embolic filter; and determining an efficacy of the embolic filter at capturing the radiopaque particulates from the flow of blood by imaging the embolic filter and the radiopaque particulates in the blood vessel.

2. The method of claim 1, wherein injecting the radiopaque particulates into the flow of blood passing through the blood vessel comprises positioning a distal end of an introducer upstream from the embolic filter and injecting the radiopaque particulates into the flow of blood passing through the blood vessel through the introducer.

3. The method of claim 2, wherein positioning the embolic filter in the blood vessel comprises deploying the embolic filter in an aortic arch.

4. The method of claim 3, wherein positioning the distal end of the introducer upstream of the embolic filter comprises:

performing a partial sternotomy to provide transapical access to a heart; and inserting the distal end of the introducer into the heart.

5. The method of claim 2, wherein:

positioning the embolic filter in the blood vessel comprises inserting the embolic filter into a vasculature comprising the blood vessel through an access site; and positioning the distal end of the introducer upstream from the embolic filter comprises inserting the introducer into the vasculature through the access site.

6. The method of claim 1, wherein imaging the embolic filter and the radiopaque particulates in the flow of blood passing through the blood vessel comprises fluoroscopic imaging.

7. The method of claim 1, wherein imaging the embolic filter and the radiopaque particulates in the flow of blood passing through the blood vessel comprises echocardiographic imaging.

8. The method of claim 1, comprising:

measuring an amount of the radiopaque particulates injected into the flow of blood passing through the blood vessel; and measuring an amount of the radiopaque particulates captured by the embolic filter from the flow of blood passing through the blood vessel by evaluating images generated via the imaging the embolic filter and the radiopaque particulates in the flow of blood passing through the blood vessel.

9. The method of claim 1, comprising:

measuring an amount of the radiopaque particulates injected into the flow of blood passing through the blood vessel; and measuring an amount of the radiopaque particulates that bypass the embolic filter by evaluating images generated via the imaging the embolic filter and the radiopaque particulates in the flow of blood passing through the blood vessel.

10. The method of claim 1, wherein injecting radiopaque particulates into the flow of blood passing through the blood vessel comprises injecting a mixture of a saline solution and the radiopaque particulates into the flow of blood passing through the blood vessel.

11. The method of claim 1, wherein imaging the embolic filter and the radiopaque particulates in the flow of blood passing through the blood vessel comprises imaging at least a portion of the radiopaque particulates in the flow of blood passing through the blood vessel entering the embolic filter.

12. The method of claim 1, wherein imaging the embolic filter and the radiopaque particulates in the flow of blood passing through the blood vessel comprises imaging capture of at least a portion of the radiopaque particulates in the flow of blood passing through the blood vessel by the embolic filter.

13. A method of evaluating an embolic filter, the method comprising:

positioning an embolic filter in a blood vessel;

injecting radiopaque particulates into the blood vessel upstream of the embolic filter;

measuring an amount of the radiopaque particulates injected into the blood vessel;

measuring an amount of the radiopaque particulates captured by the embolic filter by evaluating images generated via the imaging the embolic filter and the radiopaque particulates in the blood vessel; and determining an efficacy of the embolic filter at capturing the radiopaque particulates by imaging the embolic filter and the radiopaque particulates in the blood vessel, wherein determining the efficacy of the embolic filter at capturing the radiopaque particulates is based on the measured amount of the radiopaque particulates captured by the embolic filter.

14. The method of claim 13, wherein injecting the radiopaque particulates into the blood vessel comprises positioning a distal end of an introducer upstream from the embolic filter and injecting the measured amount of the radiopaque particulates into the blood vessel through the introducer.

15. The method of claim 14, wherein positioning the distal end of the introducer upstream of the embolic filter comprises:

performing a partial sternotomy to provide transapical access to a heart; and inserting the distal end of the introducer into the heart.

16. The method of claim 13, wherein the measured amount of the radiopaque particulates is measured by imaging the embolic filter and the radiopaque particulates in the blood vessel with at least one of fluoroscopic imaging and echocardiographic imaging.

17. A method of evaluating an embolic filter, the method comprising:

positioning an embolic filter in a blood vessel;

injecting radiopaque particulates into the blood vessel upstream of the embolic filter;

measuring an amount of the radiopaque particulates injected into the blood vessel;

measuring an amount of the radiopaque particulates that bypass the embolic filter by evaluating images generated via the imaging the embolic filter and the radiopaque particulates in the blood vessel; and determining an efficacy of the embolic filter at capturing the radiopaque particulates by imaging the embolic filter and the radiopaque particulates in the blood vessel, wherein determining the efficacy of the embolic filter at capturing the radiopaque particulates is based on the measured amount of the radiopaque particulates that bypasses the embolic filter.

18. The method of claim 17, wherein injecting the radiopaque particulates into the blood vessel comprises positioning a distal end of an introducer upstream from the embolic filter and injecting the radiopaque particulates into the blood vessel through the introducer.

19. The method of claim 18, wherein positioning the distal end of the introducer upstream of the embolic filter comprises:

performing a partial sternotomy to provide transapical access to a heart; and inserting the distal end of the introducer into the heart.

20. The method of claim 17, wherein measuring the amount of the radiopaque particulates that bypass the embolic filter comprises imaging the embolic filter and the radiopaque particulates in the blood vessel with at least one of fluoroscopic imaging and echocardiographic imaging.

* * * * *